United States Patent
Yamazaki

(10) Patent No.: US 12,207,867 B2
(45) Date of Patent: Jan. 28, 2025

(54) LIGHT IRRADIATION BEAUTY DEVICE

(71) Applicant: YA-MAN LTD., Tokyo (JP)

(72) Inventor: Iwao Yamazaki, Tokyo (JP)

(73) Assignee: YA-MAN LTD., Tokyo (JP)

( * ) Notice: Subject to any disclaimer, the term of this patent is extended or adjusted under 35 U.S.C. 154(b) by 892 days.

(21) Appl. No.: 17/055,765

(22) PCT Filed: Jun. 1, 2018

(86) PCT No.: PCT/JP2018/021164
§ 371 (c)(1),
(2) Date: Nov. 16, 2020

(87) PCT Pub. No.: WO2019/229973
PCT Pub. Date: Dec. 5, 2019

(65) Prior Publication Data
US 2021/0228273 A1    Jul. 29, 2021

(51) Int. Cl.
| | | |
|---|---|---|
| *A61B 18/20* | (2006.01) | |
| *A45D 26/00* | (2006.01) | |
| *A61B 18/18* | (2006.01) | |
| *A61B 17/00* | (2006.01) | |
| *A61B 18/00* | (2006.01) | |

(52) U.S. Cl.
CPC .......... *A61B 18/18* (2013.01); *A45D 26/0033* (2013.01); *A45D 2200/205* (2013.01); *A61B 2017/00075* (2013.01); *A61B 2018/00017* (2013.01); *A61B 2018/00202* (2013.01); *A61B 2018/00476* (2013.01); *A61B 2018/00642* (2013.01); *A61B 2018/00767* (2013.01); *A61B 2018/1807* (2013.01); *A61B 18/203* (2013.01)

(58) Field of Classification Search
CPC .......................... A61B 18/203; A61N 5/0616
See application file for complete search history.

(56) References Cited

U.S. PATENT DOCUMENTS

| | | | |
|---|---|---|---|
| 6,758,845 B1* | 7/2004 | Weckwerth | A61B 18/203 606/9 |
| 2002/0049432 A1* | 4/2002 | Mukai | A61B 18/203 606/9 |
| 2008/0119829 A1 | 5/2008 | Okawa | |
| 2012/0010684 A1* | 1/2012 | Owens | A61N 5/0616 607/88 |
| 2014/0005644 A1* | 1/2014 | Karni | A61B 18/203 606/9 |

(Continued)

FOREIGN PATENT DOCUMENTS

| | | |
|---|---|---|
| CN | 106806995 A | 6/2017 |
| JP | 2008-119419 A | 5/2008 |

(Continued)

OTHER PUBLICATIONS

Office Action dated Mar. 1, 2022 issued by the Japanese Patent Office in Japanese Application No. 2020-522538.

(Continued)

*Primary Examiner* — Lynsey C Eiseman
(74) *Attorney, Agent, or Firm* — Sughrue Mion, PLLC

(57) ABSTRACT

A beauty device (1, 2, 3) includes rollers (220, 226-1, 226-2), at least one part of which is in contact with skin and a center portion and an end portion of which have different diameters, an irradiation unit (212) that irradiates the skin with light, and a control unit (130, 315, 135, 316) that controls the irradiation unit based on the rotation of the rollers.

20 Claims, 12 Drawing Sheets

(56) References Cited

U.S. PATENT DOCUMENTS

| | | | |
|---|---|---|---|
| 2014/0214014 A1* | 7/2014 | Yamazaki | A61B 18/203 606/9 |
| 2014/0257254 A1* | 9/2014 | Boutoussov | A61B 18/203 606/9 |
| 2016/0106505 A1* | 4/2016 | Speelpenning | A61B 5/441 606/131 |
| 2016/0257008 A1* | 9/2016 | Sato | B26B 19/048 |

FOREIGN PATENT DOCUMENTS

| | | |
|---|---|---|
| JP | 2012-239874 A | 12/2012 |
| JP | 2016-163657 A | 9/2016 |
| JP | 2018-033923 A | 3/2018 |

OTHER PUBLICATIONS

Communication dated Dec. 16, 2020, from The China National Intellectual Property Administration in Application No. 201880000842.3.

International Search Report for PCT/JP2018/021164 dated Jul. 24, 2018 [PCT/ISA/210].

Written Opinion for PCT/JP2018/021164 dated Jul. 24, 2018 [PCT/ISA/237].

* cited by examiner

LIGHT IRRADIATION BEAUTY DEVICE

CROSS REFERENCE TO RELATED APPLICATIONS

This application is a National Stage of International Application No. PCT/JP2018/021164 filed Jun. 1, 2018, the entire contents of which is herein incorporated by reference in its entirety.

TECHNICAL FIELD

The present invention relates to a beauty device that performs light irradiation.

BACKGROUND ART

Conventionally, a device is known for irradiating a user's skin with light to perform a treatment that makes the user's body hair inconspicuous relative to their skin surface (depilation treatment), (for example, see Patent Document 1).

Such a light irradiation beauty device partially burns body hair or damages hair roots by irradiation of light by a flash lamp. The burned body hair becomes fragile, and thus can be easily removed from the skin surface. Damage of the hair roots suppresses regrowth of the body hair.

CITATION LIST

Patent Documents

Patent Document 1: Japanese Patent Application Laid-Open No. 2012-239874

SUMMARY OF THE INVENTION

Problems to be Solved by the Invention

When a general user performs skin care using the beauty device described above, desired effects may fail to be obtained if the user operates the beauty device inappropriately. For example, if the user operates the beauty device without care, there may result areas of skin that are not irradiated with light (unevenness). On the contrary, if the user operates the beauty device with excessive care, there is a possibility that a same skin area may be subject to more irradiation than intended.

It is an object of the present invention to support operation by a user of a light irradiation beauty device.

Means for Solving the Problems

In one aspect, the present invention provides a beauty device that includes rollers, at least a part of which is in contact with skin, and a center portion and an end portion having different diameters; an irradiation unit for irradiating the skin with light; and a control unit for controlling the irradiation unit based on rotation of the rollers.

MODE FOR CARRYING OUT THE INVENTION

First Embodiment

Figure 1:
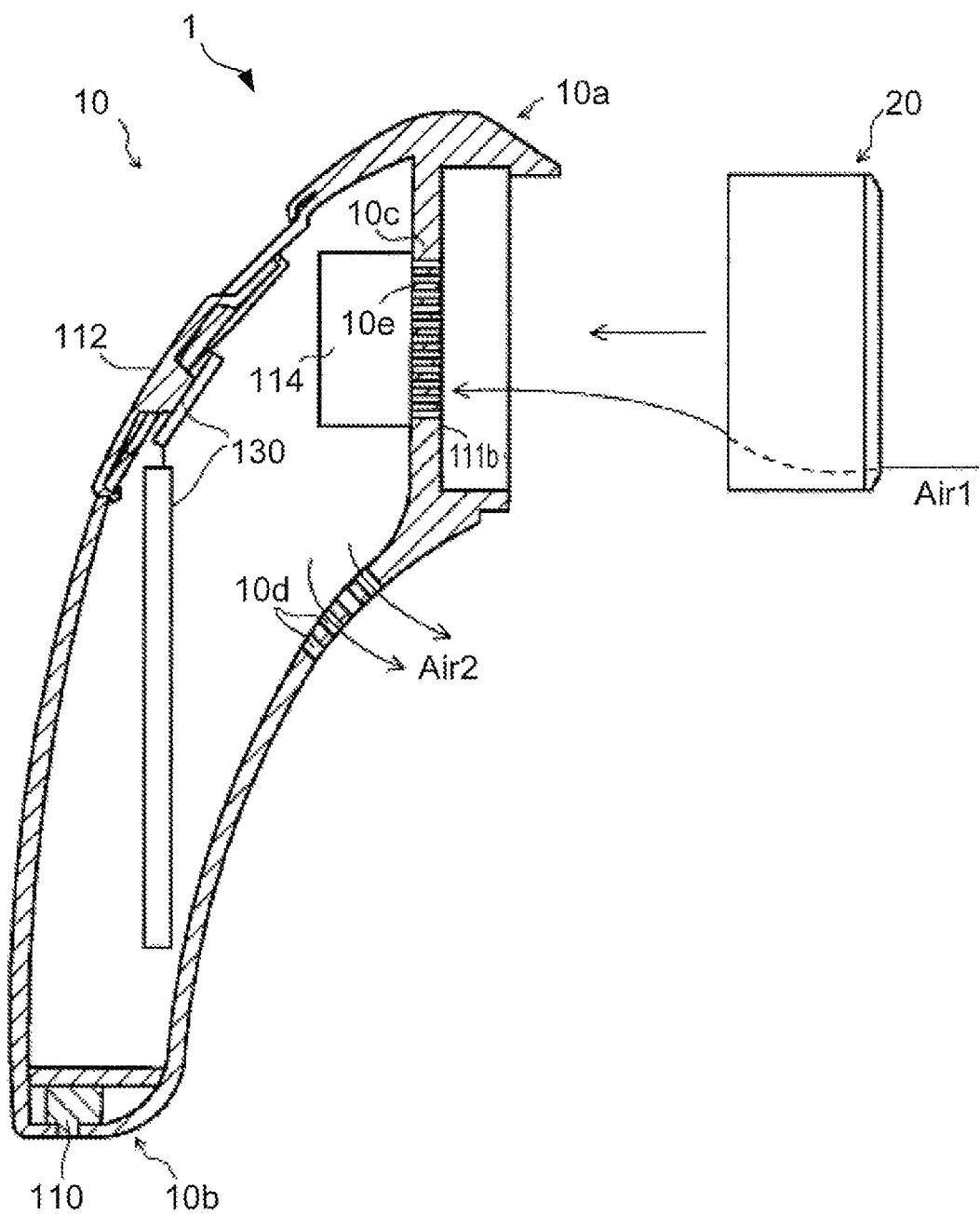
FIG. 1 is a schematic view of a light irradiation beauty device 1 of a first embodiment.

As illustrated in FIG. 1, a light irradiation beauty device 1 of a first embodiment includes a device body 10 and a light irradiation unit 20.

The light irradiation beauty device 1 is a device for performing depilation treatment. The light irradiation beauty device 1 irradiates a user's body (for example, a face, hand, leg, or the like) with high luminance light from the light irradiation unit 20 to burn the body hair for removal, and damage hair roots to suppress growth or regeneration of the body hair.

The light irradiation beauty device 1 continuously irradiates a user's skin with the light of the light irradiation unit 20 while being moved on the skin surface by the user.

(Device Body 10)

The device body 10 includes a tip end portion 10a, a rear end portion 10b, a partition unit 10c, and vents 10d and 10e. In the device body 10 there are disposed a terminal unit 110, an operation unit 112, a cooling fan 114, and a control board 130.

The device body 10 may also include a chargeable secondary battery, a power cable for inputting power of the secondary battery or power from a commercial power source or the like into the light irradiation unit 20, or may also include a cable for transmitting or receiving a signal for controlling light irradiation timing of the light irradiation unit 20.

In the device body 10, corner units are generally rounded so that a user can easily hold the device body 10 with one hand. The device body 10 has a gently curved shape overall (a substantially circular arc shape as a whole).

To the tip end portion 10a, the light irradiation unit 20 is detachably attached. Although not illustratively described herein, the tip end portion 10a includes a holding mechanism for holding the light irradiation unit 20.

The holding mechanism is not particularly limited insofar as the light irradiation unit 20 is prevented from becoming easily detached from the tip end portion 10a. The holding mechanism may, for example, comprise a magnet. In this case, it is desirable that at least a part of the light irradiation unit 20 is formed from a metal. The tip end portion 10a and the light irradiation unit 20 may include magnets of opposite polarities.

In the rear end portion 10b, the terminal unit 110 is exposed.

The partition unit 10c is located in the tip end portion 10a inside the device body 10. The partition unit 10c faces the attached light irradiation unit 20. Although not shown, a contact terminal for electrical connection of the light irradiation unit 20 is disposed in the partition unit 10c. The holding mechanism described above may be provided in the partition unit 10c.

The vents 10d penetrate from the front surface to the rear surface of the device body 10. The vents 10d are exhaust ports.

The vents 10e penetrate from the front surface to the rear surface of the partition unit 10c. In this embodiment, the vents 10d are inlet ports.

The terminal unit 110 is provided to connect the light irradiation beauty device 1 to a commercial power source. The commercial power source enables the light irradiation unit 20 to emit light and/or enables charging of the secondary battery. The terminal unit 110 is connected to the control board 130 by a cable, not shown.

The operation unit 112 has switches and a display, for example. The operation unit 112 is provided on the front surface of the device body 10. The operation unit 112 is located on the opposite side to the vents 10d. The switches include a main switch for a user to turn ON/OFF a main power source of the light irradiation beauty device 1, a light irradiation switch, and an operation mode switching switch, for example.

When a user operates the light irradiation switch, the user can manually emit light from the light irradiation unit 20 at a desired timing.

When a user operates the operation mode switching switch, the user can change an operative light irradiation intensity of the light irradiation unit 20, or prevent use of (a function of) the light irradiation switch.

The display includes a Light Emitting Diode (LED) or a liquid crystal display, for example. The display enables a user to know a present operating mode of the light irradiation beauty device 1.

The cooling fan 114 is a sirocco fan or a turbo fan, for example. The cooling fan 114 draws outside air into the device body 10 through the light irradiation unit 20 attached to the tip end portion 10a and the vents 10e (see "Air 1" in the figure). The air drawn into the device body 10 is exhausted via the vents 10d (see "Air 2" in the figure).

(Light Irradiation Unit 20)

Figure 2:
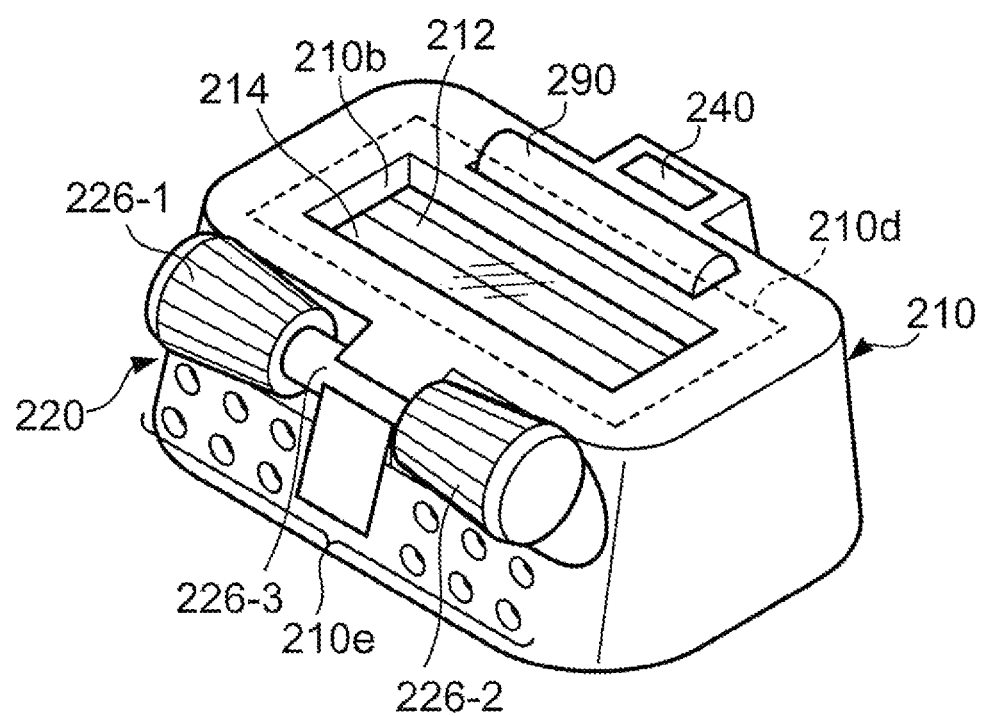
FIG. 2 is a perspective view of a light irradiation unit 20.
Figure 3A:
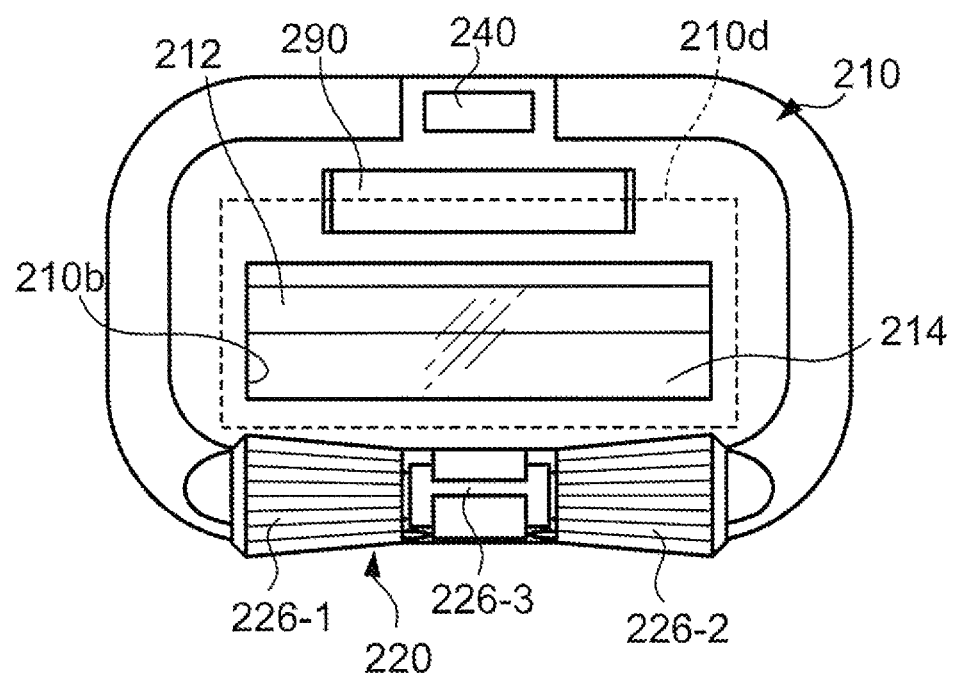
FIG. 3A is a bottom view of the light irradiation unit 20.

As illustrated in FIG. 2 and FIG. 3A, the light irradiation unit 20 includes a chassis 210 (a body having a first surface in contact with the skin surface), a xenon tube 212 (light emitting element), a transparent glass 214, a main roller 220 (first roller), an imaging unit 240, and an auxiliary roller 290 (second roller).

The light irradiation unit 20 irradiates skin with light from the xenon tube 212.

The light irradiation unit 20 is configured to be detachably attached to the device body 10. By this configuration, when the xenon tube 212 deteriorates over time, for example, the light irradiation unit 20 can be replaced.

The chassis 210 includes a skin contact surface (first surface), an opening 210b (an opening provided in the body having the first surface), a touch sensor unit 210d (contact detection means), an imaging unit 240, and vents 210e. The chassis 210 houses the xenon tube 212, the transparent glass 214, the auxiliary roller 290, and the main roller 220.

The imaging unit 240 includes optical systems, such as a camera and a lens; and analysis systems, such as a light receiving element and an image processing processor. The imaging unit 240 images the skin contact surface to acquire image data, performs image processing (for example, generation of feature information indicating a color tone, condition, and the like of the skin) as necessary, and then outputs image processing results.

The skin contact surface is the front surface of the chassis 210 and contacts the skin surface of a user in depilation treatment. Preferably, the skin contact surface is coated with glass, plastic, or the like to facilitate smooth movement on the skin surface of the user.

The opening 210b is provided from the skin contact surface toward the inside of the chassis 210. Light emitted by the xenon tube 212 passes through the opening 210b and is guided to the skin. The shape of the opening 210b is substantially rectangular.

The long side of the opening 210b is along the rotation axis direction of the main roller 220 rotatably provided to be partially exposed from the first surface.

The length of the short side of the opening 210b is the "length of the width along a direction orthogonal to the rotation axis of the main roller 220." Herein, the description "along a direction orthogonal to the rotation axis of the main roller 220" has the same meaning as the description "along the movement direction of the light irradiation beauty device 1."

The touch sensor unit 210d is a part around the opening 210b of the skin contact surface. The touch sensor unit 210d includes a capacitive touch sensor, for example. The capacitive touch sensor may be either a surface type or a projection type. The touch sensor is electrically connected to the control board 130.

When a skin surface of a user contacts the touch sensor unit 210d, a current flows between the touch sensor and the control board 130, or a voltage is applied therebetween. The control board 130 detects the current or the voltage and thereby detects whether the skin surface of a user is in contact with the circumference of the opening 210b. The touch sensor unit 210d may include an electronic circuit to convert the current or the voltage into a digital signal and output the digital signal to the control board 130. The touch sensor unit 210d may output a signal indicating a presence or absence of the contact. For example, Presence of contact: 1 and Absence of contact: 0 are referred to.

The touch sensor is not particularly limited so long as contact of the skin surface of a user can be detected. The touch sensor unit 210d can include touch sensors of various systems, such as a resistance film system, a surface acoustic wave system, an infrared system, and an electromagnetic induction system, for example. Further, the touch sensor unit 210d can also include an illuminance sensor for detecting illuminance in the opening 210b. The illuminance sensor detects variance in illuminance in the opening 210b upon closure of the opening due to contact with a user's skin, for example. The control board 130 can detect whether the skin surface of the user contacts the touch sensor unit 210d based on the detected illuminance.

The vents 210e penetrate from the front surface to the rear surface of the chassis 210. The vents 10d are inlet ports. By driving the cooling fan 114 of the device body 10, the outside air flows into the chassis 210 from the vents 210e, and into the device body 10. The inflowing air cools the xenon tube 212.

The xenon tube 212 is provided in the opening 210b.

The transparent glass 214 is fitted into the opening 210b. The transparent glass 214 cuts (reduces a wavelength range of ultraviolet rays) ultraviolet rays included in light of the xenon tube 212. The transparent glass 214 prevents a user from inadvertently putting a finger or the like into the opening 210b.

The auxiliary roller 290 is a long and thin barrel-shaped roller a diameter of which at both ends is smaller than that at the center. When a user moves the device body 10 in a vertical direction in the sheet surface of FIG. 3A while applying the device body 10 to a skin contact surface, the auxiliary roller 290 rotates around an axis arranged in the horizontal direction on the same sheet surface. Under rotation of the auxiliary roller 290, the device body 10 is able to smoothly move on the skin contact surface. The shape of the auxiliary roller 290 may be a cylinder without being limited to a barrel. In a preferred aspect, the shape may be one that facilitates stable movement in a specific direction (vertical direction on the sheet surface in this example). The rotation axis of the auxiliary roller 290 is preferably the same as that of the main roller 220. More specifically, the rotation axis of the auxiliary roller 290 is preferably provided in parallel to the longitudinal direction of the opening 210b. Further, in a preferred aspect, the auxiliary roller 290 is not formed to process irregularities, and thus is smooth. Hence, when a user moves the device body 10 in a skin contact state the user can easily change the direction of movement from the rotation direction (vertical direction on the sheet surface) to a direction different therefrom (a direction having a horizontal direction component on the sheet surface).

Figure 3B:
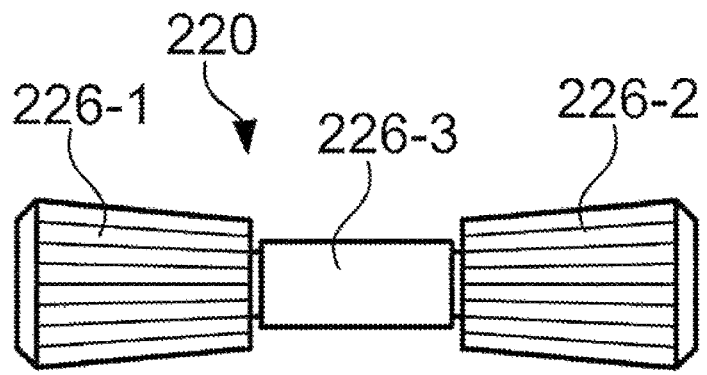
FIG. 3B is an enlarged schematic view of a main roller 220.

As illustrated in FIG. 3A and FIG. 3B, the main roller 220 is provided on the opposite side to the auxiliary roller 290 with the opening 210b interposed therebetween. The main roller 220 has a center portion 226-3 fixed to the chassis 210 and a left roller 226-1 and a right roller 226-2 arranged on both sides of the center portion 226-3. The surfaces of the left roller 226-1 and the right roller 226-2 are preferably subject to an anti-slip treatment.

At least one part of the main roller 220 contacts skin, with different diameters at the center portion and the end portions. More specifically, the diameter gradually increases toward the outside from the center portion on the rotation axis. As a result, stability of straight travel is enhanced.

Figure 3C:
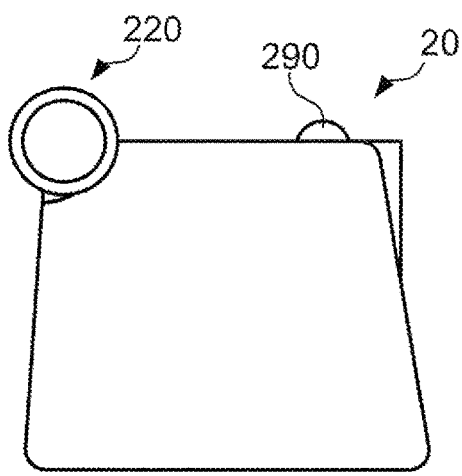
FIG. 3C is a side view of the light irradiation unit 20.

Further, as illustrated in FIG. 3C, it is preferable that a height projection from the skin contact surface of the main roller 220 is greater than the height projection from the skin contact surface of the auxiliary roller 290, as viewed from the side. In addition, it is preferable that the radius of rotation (average radius of rotation) of the main roller 220 is greater than the radius of rotation (average radius of rotation) of the auxiliary roller 290. In other words, although, when the skin contact surface is pressed against skin in parallel thereto, the skin can contact both the main roller 220 and the auxiliary roller 290 because the skin has elasticity, and an arrangement by which the main roller 220 firmly (with high adhesion) contacts the skin is preferable. Thus, there are achieved both stability of straight travel, which is largely due to the structure of the main roller 220, and flexibility of directional change, which is largely due to provision of the auxiliary roller 290.

Further, a user can change a distribution of pressure applied to the main roller 220 and the auxiliary roller 290 by adjusting an angle of inclination between the skin contact surface and skin and/or a degree of force applied (abutting force; closeness degree), as appropriate. As a result, stability of straight travel and flexibility of directional change inherent to the device body 10 can be adjusted as appropriate.

The shape and the arrangement of the main roller 220 and the auxiliary roller 290 disclosed in FIG. 2, FIG. 3A, FIG. 3B, and FIG. 3C are examples only. For example, the diameter of the left roller 226-1 and the right roller 226-2 may decrease from the center toward the outside as is the case with the auxiliary roller 290.

Conversely, the diameter of the auxiliary roller 290 may increase from the center toward the outside.

In short, because two rollers having different functions and roles can contact skin, operability is improved.

(Main Roller 220)

Figure 4:
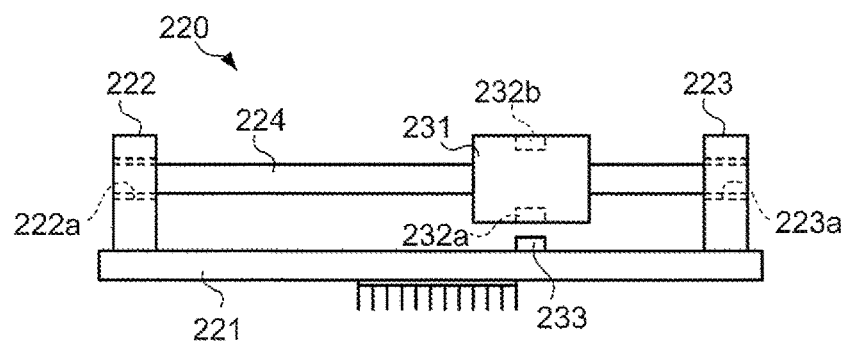
FIG. 4 is an internal structure view of the main roller 220.
Figure 5:
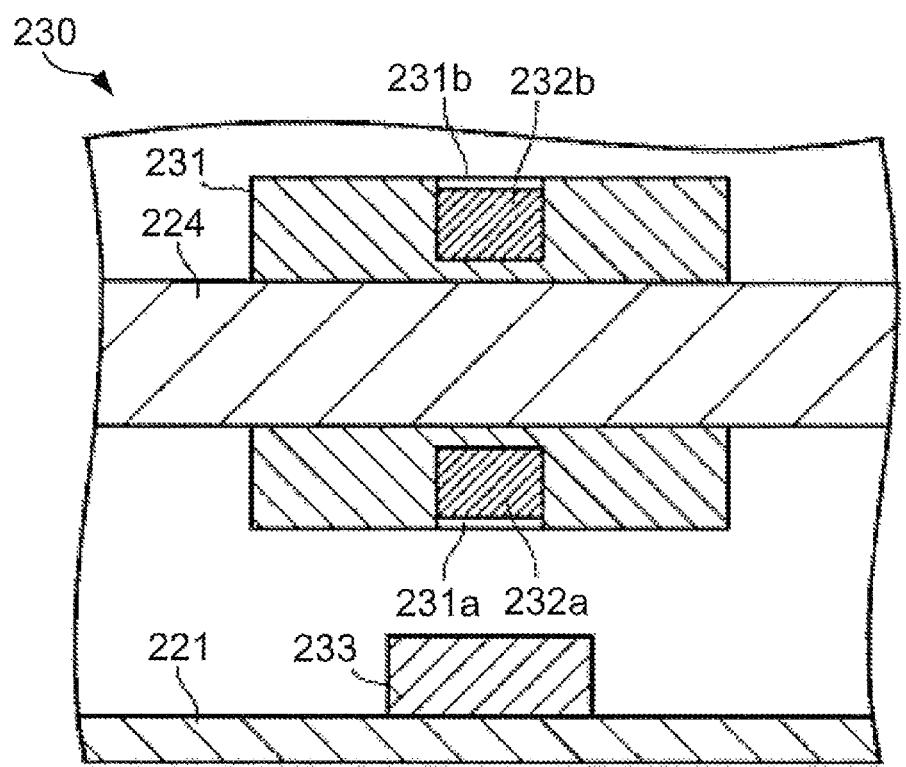
FIG. 5 is an enlarged cross-sectional view illustrating a part of a detection unit 230.

As illustrated in FIG. 4 and FIG. 5, the main roller 220 includes a board 221, shaft-holding stands 222, 223, a rotation shaft 224, and a detection unit 230 (signal output means) as internal structures. The left roller 226-1 and the right roller 226-2 are connected to the rotation shaft 224, but are not shown in the figures.

The board 221 holds the shaft-holding stands 222, 223, the rotation shaft 224, the left roller 226-1, the right roller 226-2, and the detection unit 230. On the board 221, an electronic circuit connected to the detection unit 230 is formed. The electronic circuit includes a connection pin 221a for transmitting or receiving a signal. The electronic circuit includes electronic devices (for example, an IC chip, resistive element, capacitor, and coil element), which are not shown.

The shaft-holding stands 222, 223 are columns. The shaft-holding stands 222, 223 are provided on the board 221. The shaft-holding stands 222, 223 face each other at a predetermined distance from each other. The shaft-holding stands 222, 223 are arranged apart from each other along the long side of the opening 210b illustrated in FIG. 2.

The shaft-holding stand 222 includes through-holes 222a.

The through-holes 222a are arranged in successive series from the bottom (board 221 side) toward the top. The rotation shaft 224 is rotatably inserted into the through-holes 222a.

The shaft-holding stand 223 includes through-holes 223a. The through-holes 223a are arranged in series from the bottom (board 221 side) toward the top. The positions where the through-holes 223a are disposed (height from the board 221) correspond to the positions of the through-holes 222a.

The rotation shaft 224 is rotatably inserted into the through-holes 223a.

The length in the longitudinal direction of the rotation shaft 224 is greater than the distance between the shaft-holding stands 222, 223. As a result, the right and left ends of the rotation shaft 224 are located outside the shaft-holding stands 222, 223, respectively.

In parts located outside the shaft-holding stands 222, 223, locking members, which are not shown, are provided. The locking members prevent the rotation shaft 224 from detaching from the shaft-holding stands 222, 223. Any locking member is acceptable without being particularly limited so long as it is structured so that detachment can be prevented. The locking member is a flange or a nut having a diameter larger than the diameters of the through-holes 222a and 223a, for example. Detachment is prevented by a flange or a nut being fixedly-fitted in the shaft-holding stands 222, 223.

(Detection Unit 230)

The detection unit 230 includes a holding unit 231, detection targets 232a, 232b, and a sensor 233.

The holding unit 231 is provided on the rotation shaft 224. The holding unit 231 and the rotation shaft 224 rotate integrally with each other.

As illustrated in FIG. 5, the holding unit 231 includes holding holes 231a, 231b. The holding unit 231 houses the detection targets 232a, 232b. The holding unit 231 has a cylindrical shape.

The holding holes 231a, 231b each are provided in each of the side surfaces of the holding unit 231. The holding holes 21a and 231b are provided from the side surfaces of the holding unit 231 toward a center portion of the holding unit 231. The holding holes 231a, 231b are shifted from each other by 180° in the circumferential direction of the holding unit 231. More specifically, the two holding holes 231a, 231b are positioned opposite each other with the rotation shaft 224 interposed therebetween.

The detection targets 232a, 232b are disposed in the holding holes 231a, 231b, respectively. The detection targets 232a, 232b are magnets, for example. Herein, the detection targets 232a, 232b are neodymium magnets.

The sensor 233 is fitted at a position on the board 221 that corresponds to the holding unit 231. The sensor 233 detects the magnetic fields of the detection targets 232a, 232b. A signal (current or voltage) corresponding to the magnetic field strength detected by the sensor 233 flows between the sensor 233 and the control board 130 or is applied therebetween.

Herein, "flows between the sensor 233 and the control board 130 or is applied therebetween" is used to mean "the detection unit 230 outputs a signal to the control board 130." The control board 130 controls light emission of the xenon tube 212 based on the output of the signal.

The sensor 233 includes a Hall element, for example. The control board 130 detects a voltage generated in the Hall element.

The sensor 233 may include an electronic circuit, and convert a current or a voltage into a digital signal and output the digital signal to the control board 130. The sensor 233 can compare the value of a current or a voltage with a predetermined threshold. The sensor 233 may output a digital signal indicating that the detection targets 232a, 232b are detected to the control board 130 as a result of the comparison. For example, when a value of the current or the voltage of the sensor 233 is equal to or greater than a threshold, a signal indicating "1: Detection of detection target" is output. When a value of the current or the voltage of the sensor 233 is smaller than the threshold, a signal indicating "0: Non-detection of detection target" is output.

In the main roller 220 configured as described above, the rotation shaft 224 and the holding unit 231 rotate under rotation of the left roller 226-1 or the right roller 226-2. Although the rotation shafts of the left roller 226-1 and the right roller 226-2 are common in this example, the rotation shafts may be separately provided in each of the left roller 226-1 and the right roller 226-2. More specifically, the left roller 226-1 and the right roller 226-2 may be configured to be independently rotatable. In this case, with respect to the light emission control corresponding to the number of rotations, described later, the sensor may be provided only in one of the rotation shafts or may be provided in both of the rotation shafts. In the latter case, statistical processing (calculation of an average value or the like) of the selection of either of the rotations is performed for the two measured numbers of rotations, and then a signal indicating the number of rotations of the main roller 220 can be output.

When the holding unit 231 rotates, the detection target 232a approaches the sensor 233. The sensor 233 detects the magnetic field of the detection target 232a. Further, when the holding unit 231 rotates (herein, 180° rotation), the detection target 232b approaches the sensor 233 at this time. The sensor 233 detects the magnetic field of the detection target 232b at this time.

In response to the rotation of the holding unit 231, the sensor 233 repeatedly outputs a signal detecting the detection target 232a and a signal detecting the detection target 232b, in that order, to the control board 130. Upon the signal input into the control board 130, the xenon tube 212 emits light.

(Relationship Between Holding Unit 231 and Opening 210b)

Figure 6:
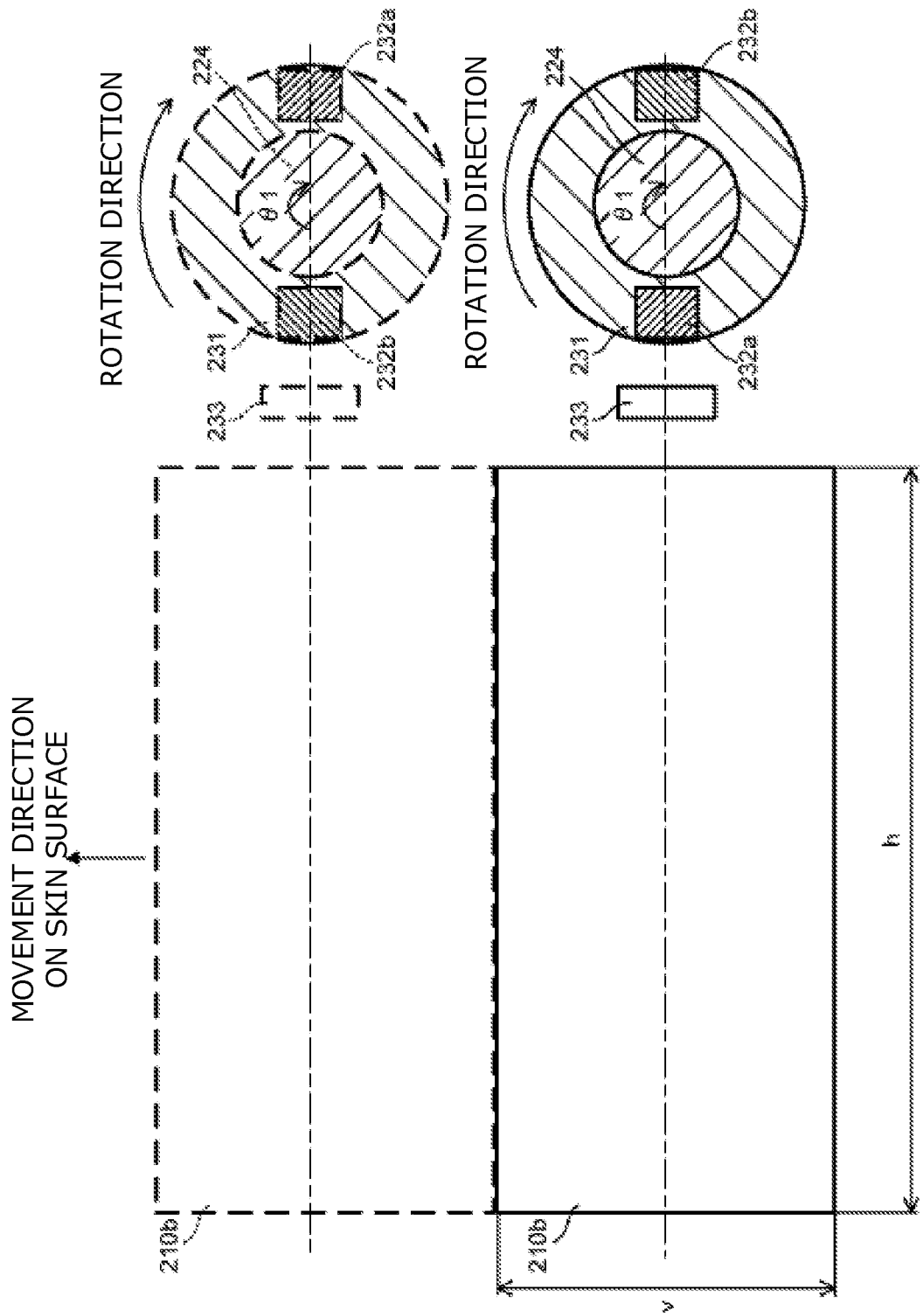
FIG. 6 is a view schematically illustrating a holding unit 231 and an opening 210b.

Next, the relationship between the holding unit 231 and the opening 210b of the device body 10 is described with reference to FIG. 6. FIG. 6 shows a cross section of the holding unit 231 and illustrates the opening 210b from the front.

The alternate long and short dash lines in the figure are virtual lines illustrating that the opening 210b, the sensor 233, and the holding unit 231 illustrated by the solid lines correspond to each other, and the opening 210b, the sensor 233, and the holding unit 231 illustrated by the dashed lines correspond to each other.

The opening 210b has a dimension of longitudinal width v [m]×lateral width h [m]. The longitudinal width v [m] is the length of the short side of the opening 210b. The lateral width h [m] is the length of the long side of the opening 210b.

The cross section of the holding unit 231 has a circular shape with a length c [m] of the circumference (not illustrated).

Herein, the relationship between the length of the circumference of the holding unit 231 and the longitudinal width of the opening 210b is represented by Expression 1 below.

$$v = c/a \qquad (1)$$

v: Longitudinal width of opening 210b
c: Length of circumference of holding unit 231
a: Variable One of the longitudinal width v and the length c of the circumference may have an error of several [m] relative to the other side. The variable a is a number greater than 0. Herein, the variable a is 2, which corresponds to the number of the detection targets.

"c/2" defines the length of the semicircle of the holding unit 231. More specifically, "c/2" defines that the length of the semicircle of the holding unit 231 is substantially equal to the longitudinal width v. When the holding unit 231 rotates in correspondence to the length of the semicircle, the light irradiation beauty device 1 is moved in correspondence to the longitudinal width v [m] of the opening 210b on the skin surface of a user.

Next, a number of detection targets and a rotation angle θ1 of the holding unit 231 required for light emission of the xenon tube 212 in this embodiment are described.

The number of detection targets and the rotation angle θ1 of the holding unit 231 required for the light emission of the xenon tube 212 are represented by Expression 2 below.

$$\theta 1 = 360/a \qquad (2)$$

θ1: Rotation angle required for first light emission to second light emission of xenon tube 212
a: Number of detection targets Herein, the number of detection targets is 2 (detection targets 232a, 232b). Therefore, the rotation angle required for the first light emission to the second light emission is 180°.

When the holding unit 231 rotates in correspondence to the rotation angle θ1, the light irradiation beauty device 1 is moved in correspondence to the longitudinal width v [m] of the opening 210b on the skin surface of a user.

(Control Board 130)

Figure 7:
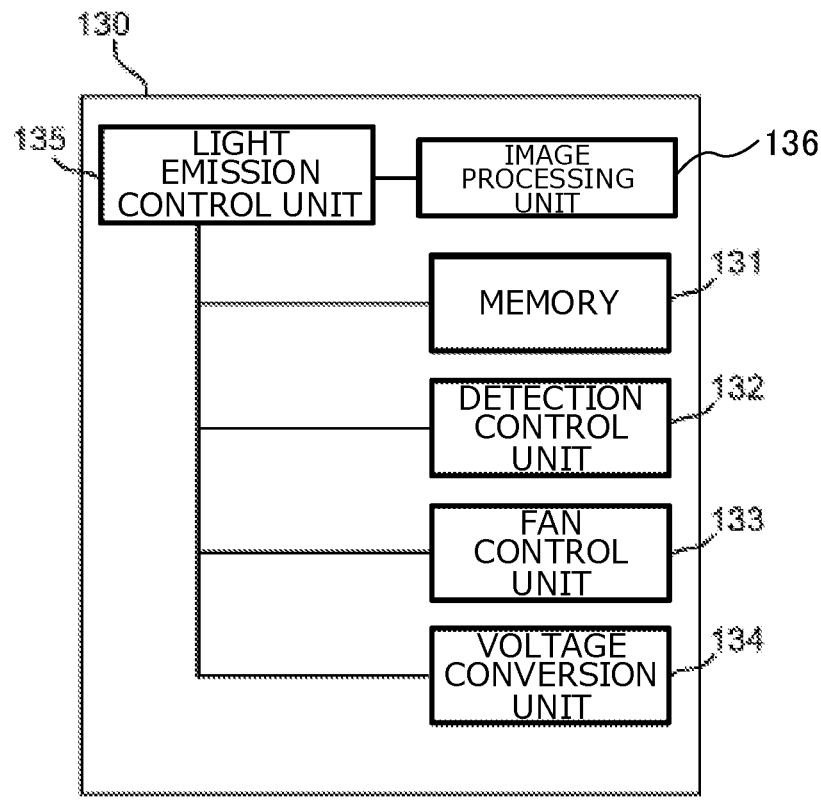
FIG. 7 is a functional block diagram of a control board 130.

Next, a function of the control board 130 is described with reference to FIG. 7. FIG. 7 is a functional block diagram of the control board 130.

As illustrated in FIG. 7, the control board 130 has a memory 131, a detection control unit 132, a fan control unit 133, a voltage conversion unit 134, an image processing unit 136 (equivalent to the imaging unit 240), and a light emission control unit 135. Functions thereof are realized by circuit elements (for example, IC chips for calculation and memory, a resistive element(s), a capacitor(s), and a coil element(s)). The control board 130 may also include a charge circuit for a secondary battery.

In the memory 131 there are pre-stored firmware, various thresholds, a conversion table, and the like.

The detection control unit 132 is connected to the operation unit 112 illustrated in FIG. 1, the touch sensor unit 210d illustrated in FIG. 2, and the detection unit 230 illustrated in FIG. 5. The detection control unit 132 detects an operation of the operation unit 112 made by a user. An analog or digital signal output from the touch sensor unit 210d or the detection unit 230 is input to the detection control unit 132.

The detection control unit 132 can also detect a voltage generated in a Hall element when the detection unit 230 includes the Hall element.

The detection control unit 132 can compare with the threshold stored in the memory 131 a voltage level or a current input from the detection unit 230 or the touch sensor unit 210d. When the current (or voltage) input from the touch sensor unit 210d is larger than the threshold, for example, the detection control unit 132 sets a "flag indicating that the skin surface of a user is in contact with the circumference of the opening 210b" (for example, a digital signal "1" is held in the memory).

When the current (or voltage) input from the detection unit 230 is larger than the threshold, for example, the detection control unit 132 sets a "flag causing the xenon tube 212 to emit light" (for example, a digital signal "1" is held in the memory). When the current (or voltage) is smaller than the threshold, a "flag causing the xenon tube 212 not to emit light" is set (for example, a digital signal "0" is held in the memory).

The flag may be set based on the digital signal (for example, the signal indicating "1: Detection of detection target" or "0: Non-detection of detection target") input from the detection unit 230 or the touch sensor unit 210d.

The fan control unit 133 is connected to the cooling fan 114 illustrated in FIG. 1. The fan control unit 133 turns ON/OFF driving of the cooling fan 114.

The voltage conversion unit 134 converts power obtained from a commercial power source or a secondary battery. The conversion unit coverts an alternating current to a direct current or boosts or drops a voltage, for example. The power converted by the voltage conversion unit 134 is used for light emission of the xenon tube 212 or the like.

The light emission control unit 135 controls the memory 131, the detection control unit 132, the fan control unit 133, and the voltage conversion unit 134.

The light emission control unit 135 includes a capacitor for temporarily storing electricity supplied to the xenon tube 212 or a charge circuit for the capacitor.

The light emission control unit 135 supplies the electricity stored in the capacitor to the xenon tube 212. As a result, the xenon tube 212 emits light.

(Light Emission Control Example 1)

The light emission control unit 135 causes the xenon tube 212 to emit light when all of the following conditions (1) to (3) are satisfied.
 (1) The "flag indicating that the skin surface of a user is in contact with the circumference of the opening 210b" is set.
 (2) The "flag causing the xenon tube 212 to emit light" is set.
 (3) Electricity required for causing the xenon tube 212 to emit light is stored in the capacitor.

(Light Emission Control Example 2)

The light emission control unit 135 also causes the xenon tube 212 to emit light when the following conditions (1) and (2) are satisfied.
 (1) The detection control unit 132 detects an operation of the operation unit 112 by a user (for example, an operation of depressing a light emitting button).
 (2) Electricity required for causing the xenon tube 212 to emit light is stored in the capacitor.

The light irradiation beauty device 1 can reduce inconvenience of operation for depilation treatment.

Herein, an example of an operation in the depilation treatment of a conventional product (hereinafter simply referred to as "device") is described. The device includes a flash lamp and an irradiation port for irradiating a skin surface with light from the flash lamp. Such a device can perform depilation treatment by 1) irradiating a skin surface to be subjected to the depilation treatment with the flash lamp light; 2) raising the device and temporarily removing the device from the skin surface; 3) causing the device to abut another skin surface to be subjected to the depilation treatment; and 4) irradiating the newly abutted skin surface with the light from the flash lamp.

In this case, the device is repeatedly raised positioned to abut a skin surface to be subjected to the depilation treatment in accordance with a number of skin surfaces be subjected to the depilation treatment.

Repeated raising and positing of the device to abut a skin surface to be subjected to the depilation treatment involves movement by a user within three dimensions, namely, a length, width and depth. Such movement may cause the device to abut a skin surface that is not the intended skin surface; and the user's hand and arm moving the device may become fatigued.

This depilation treatment method requires that a position of the irradiation port be determined for each skin surface to be subjected to the depilation treatment. However, such positioning may be time consuming if the user causes the device to abut a skin surface that is not the intended skin surface, and/or the user's hand and arm become fatigued Since the light irradiation beauty device 1 includes the main roller 220, the light irradiation beauty device can be smoothly moved in one dimension on and along a skin surface. Thus, the light irradiation beauty device 1 is prevented from abutting an unintended skin surface; and/or the user's arm used for moving the light irradiation beauty device 1 does not become fatigued As a result, the position of the opening 210b resulting from the abutment operation can be promptly determined.

In the light irradiation beauty device 1, the detection unit 230 rotates in synchronization with the rotation of the main roller 220, and the xenon tube 212 emits light whenever the light irradiation beauty device 1 moves in correspondence to the longitudinal width v [m] of the opening 210b. As a result, depilation targets can be continuously irradiated with light from the xenon tube 212 for each longitudinal width of the opening 210*b*.

As a result, unevenness in irradiation can be reduced, and a necessity for the user to depress a trigger button of the xenon tube 212 for each skin surface to be subjected to the depilation treatment can be eliminated. Further, a user need not consciously position the opening 210*b* for each skin surface to be subjected to the depilation treatment.

One meaning of irradiation unevenness is "a range of skin irradiated with light by the first light emission by the xenon tube 212 and a range of the skin surface separately irradiated with light by the second light emission by the xenon tube 212, whereby a range not irradiated with light exists." Since a depilation effect is not obtained in the range not irradiated with light, the range needs to be subject to irradiation with the light of the xenon tube 212.

Another meaning of the irradiation unevenness is "a range on the skin irradiated with light by the first light emission by the xenon tube 212 and a range on the skin surface irradiated with light by the second light emission by the xenon tube 212 overlap each other, whereby a skin surface exists that is irradiated with a greater amount of light from the xenon tube 212 than required as compared with other depilation target areas."

(Modification 1)

The light irradiation beauty device 1 of the first embodiment is described above. The light irradiation beauty device 1 can be variously modified.

The detection targets 232*a*, 232*b* and the sensor 233 may be replaced. More specifically, the holding unit 231 includes two sensors corresponding to the detection targets 232*a*, 232*b*, and the board 221 includes one detection target corresponding to the sensor 233.

The detection targets 232*a*, 232*b* may be light emitting elements (for example, LEDs). The sensor 233 may be a light receiving element (for example, a photodiode).

The light irradiation beauty device 1 may include either one of the detection targets 232*a*, 232*b*. Further, the length of the circumference of the holding unit 231 may be less than the longitudinal width of the opening 210*b*. For example, the length of the circumference of the holding unit 231 may be half the length of the longitudinal width of the opening 210*b*. In this case, the light emission control unit 135 causes the xenon tube 212 to emit light whenever the holding unit 231 rotates twice.

The detection unit 230 may be a mechanical contact sensor.

The auxiliary roller 290 may include an electrode for applying a current to the skin surface of a user. By applying a current to the skin surface of a user, muscles can be caused to be moved. As a result, an effect of removing waste or imparting "gloss" or "firmness" to skin can be expected.

The shape of the opening 210*b* may be changed (for example, to be a rectangular shape, a triangular shape, a trapezoid shape, a spherical shape, an oval shape, a star shape, and so forth).

The light irradiation beauty device 1 may include an acceleration sensor. The acceleration sensor detects movement of the light irradiation beauty device 1. The light emission control unit 135 causes the xenon tube 212 to emit light when the acceleration sensor detects such movement, namely, that "the light irradiation beauty device 1 is moved" and prevents the xenon tube 212 from emitting light when the light irradiation beauty device 1 is not moved (enhanced safety).

The device body 10 and the light irradiation unit 20 may be formed integral with each other.

The light irradiation unit 20 may include a halogen lamp or an LED lamp.

A temperature sensor may be arranged in the vicinity of the xenon tube 212. The temperature sensor is a thermistor, for example. The light emission control unit 135 causes the xenon tube 212 to emit light corresponding to a temperature of the temperature sensor. As a result, a failure of the xenon tube 212 due to occurrence of high temperature can be prevented.

An attachment with a filter covering the opening 210*b* of the light irradiation unit 20 may be attached to the chassis 210. The attachment may be attached to the chassis 210 by use of a magnet, for example. The filter is any of band pass filter, low pass filter, or high pass filter. Light of a specific wavelength can be generated and directed to the skin surface of a user. Under exposure to light of specific wavelengths, enhanced beatification of skin can be expected.

The chassis 210 and the above-described attachment may include a Peltier device. The Peltier device imparts a hot or cold sensation to a user's skin. The Peltier device can lower a temperature of skin warmed by the light of the xenon tube 212.

The device body 10, the auxiliary roller 290, or the above-described attachment may include an electrode. The electrode is used for ion introduction or ion lead-out, for example.

Ion introduction refers to a beauty method directed to penetration of vitamin C derivatives or placenta into skin layers by use of a weak current.

Ion lead-out refers to a beauty method directed to removal of dirt (for example, old keratin) from skin by applying a weak current in an opposite direction to the ion introduction direction.

For example, the electrode of the device body 10 is an anode and the electrode of the chassis 210 is a cathode. When a user holds the electrode of the device body 10 and applies the electrode of the chassis 210 to the skin surface, a weak current can be applied to the user's body.

Second Embodiment

Figure 8:
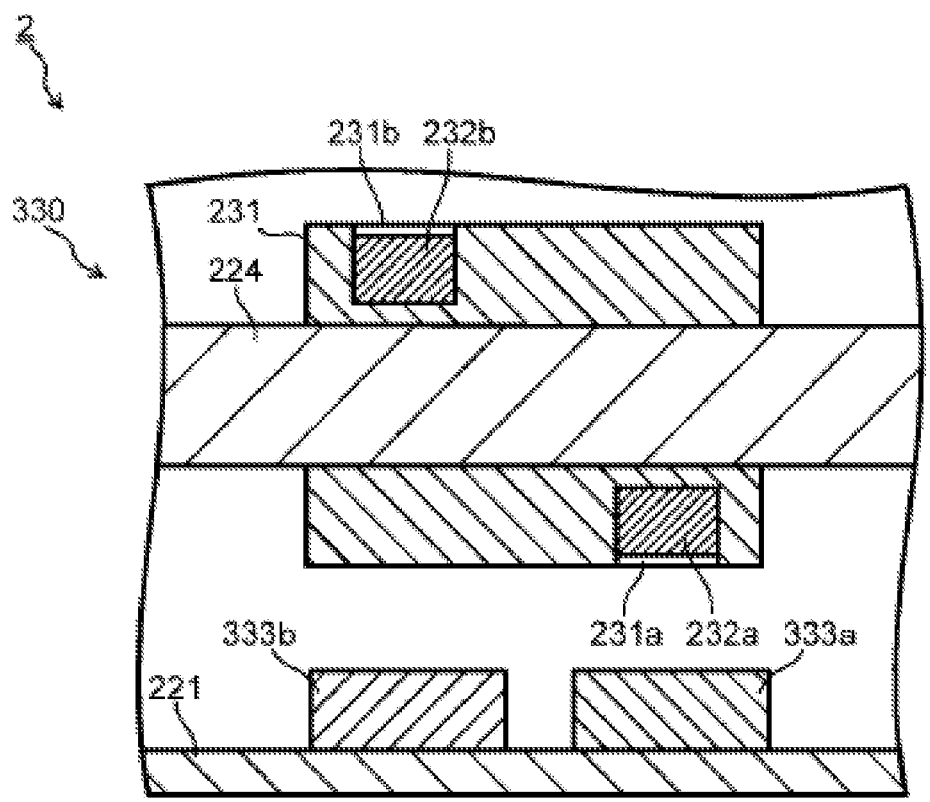
FIG. 8 is an enlarged cross-sectional view illustrating a part of a detection unit 330 of a second embodiment.

Next, a light irradiation beauty device 2 of a second embodiment of the present invention is described with reference to FIG. 8. FIG. 8 is a schematic view of a detection unit 330 (signal output means) included in the light irradiation beauty device 2 of the second embodiment.

In FIG. 8, the same constituent components as those in the first embodiment illustrated in FIG. 5 are designated by the same reference numerals and descriptions thereof are omitted.

The detection unit 330 corresponds to the detection unit 230 of the first embodiment. The detection unit 330 includes detection targets 232*a*, 232*b* and sensors 333*a*, 333*b*.

The detection targets 232*a*, 232*b* are shifted by 180° from each other in the circumferential direction of the holding unit 231, and are shifted from each other along the major axis direction (direction in which the rotation shaft 224 extends) of the holding unit 231.

The sensors 333*a*, 333*b* correspond to sensors 233*a*, 233*b*. The sensor 333 is fixed to a position on the board 221 corresponding to the detection target 232*a*. The sensor 333*a* detects a magnetic field of the detection target 232*a*.

The sensor 333*b* is fixed to a position on the board 221 corresponding to the detection target 232*b*. The sensor 333*b* detects a magnetic field of the detection target 232*b*.

In the light irradiation beauty device 2, the light emission control unit 135 (see FIG. 7) can individually identify the sensors 333a, 333b. The light emission control unit 135 causes the xenon tube 212 to emit light based on signals output from the sensors 333a, 333b.

When the light emission control unit 135 causes the xenon tube 212 to emit light based on the signal output from the sensor 333a, the light emission control unit 135 prevents the xenon tube 212 from emitting light unless a signal is subsequently output from the sensor 333b.

More specifically, when signals are successively output from the same sensor (for example, sensor 333a), the light emission control unit 135 of this embodiment prevents the xenon tube 212 from emitting light even when a signal after the second signal is input.

In some cases, the light irradiation beauty device 2 is operated to reciprocate on the skin surface. For example, the xenon tube 212 emits light once based on a signal output from the sensor 333a in the forward path.

Thereafter, the light irradiation beauty device 2 is immediately moved in an opposite direction (backward path direction).

In the backward path, the sensor 333a detects the detection target 232a, and therefore the sensor 333a continuously outputs signals of the detections in the forward path and the backward path. When the xenon tube 212 emits light based on the signal in the backward path, a skin surface irradiated with the light in the forward path is irradiated with the light of the xenon tube 212 again in a short period of time.

Since the depilation treatment has already been performed in the forward path, even when the light of the xenon tube 212 is emitted again in the backward path, the depilation effect is low in some cases. Power used for the light emission of the xenon tube 212 becomes useless in some cases.

The light irradiation beauty device 2 can reduce energy wastage.

It is desirable that control of the xenon tube 212 by the light emission control unit 135 in the light irradiation beauty device 2 can be cancelled at any time by the operation of the operation unit 112 by a user.

Although some embodiments of the present invention are described above, the embodiments and the modification are examples and are not intended to limit the scope of the invention. The novel embodiments can be implemented in various other forms and can be variously omitted, replaced, and altered without deviating from the gist of the invention. The embodiments and the modification thereof are included in the scope and the gist of the invention and are included in the invention described in the claims and any equivalent scope thereof.

Third Embodiment

Figure 9:
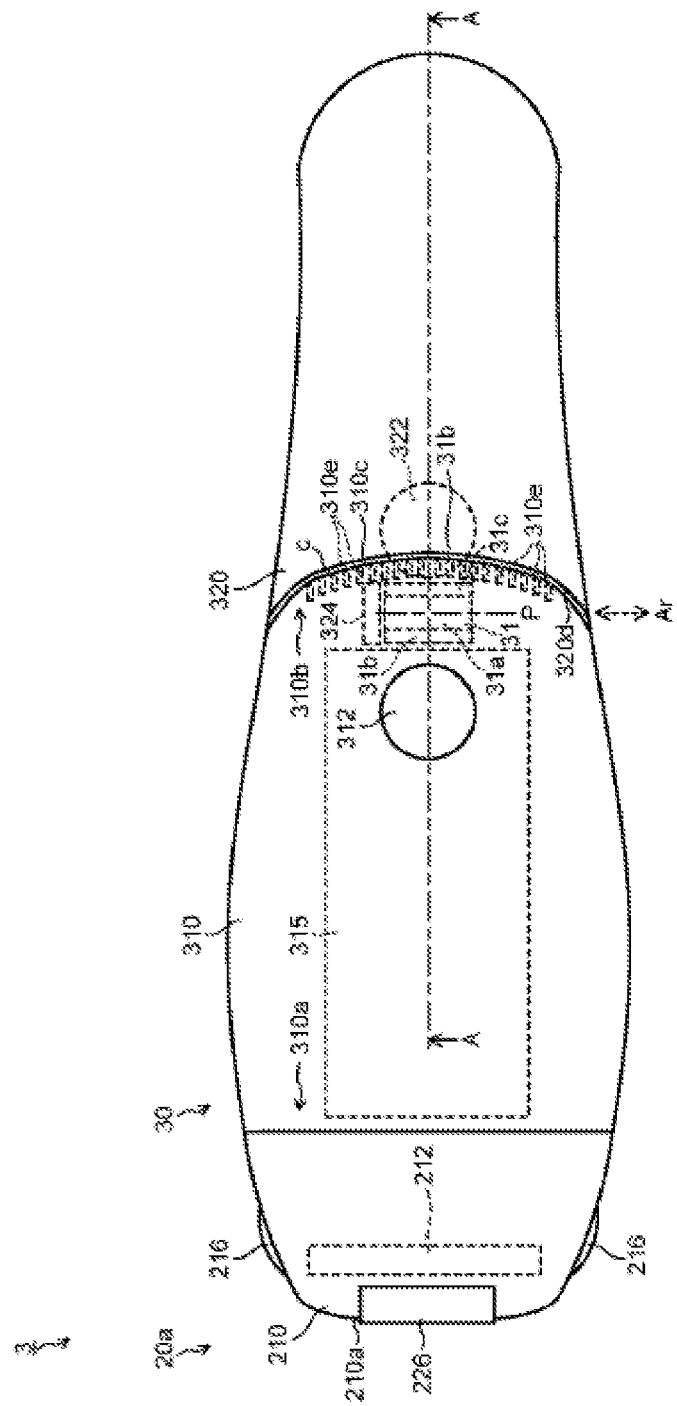
FIG. 9 is a plan view in which a light irradiation beauty device 3 is viewed with an operation unit 312 at the front.
Figure 10:
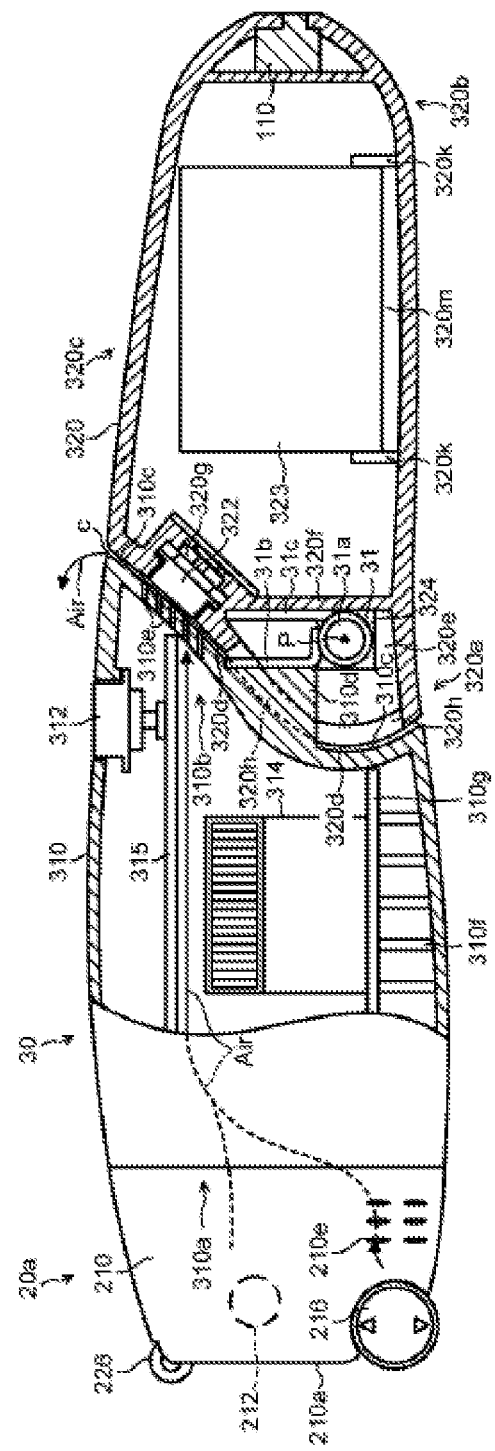
FIG. 10 is a partial cross-sectional view of the light irradiation beauty device 3 in an A-A cross section of FIG. 9.
Figure 11:
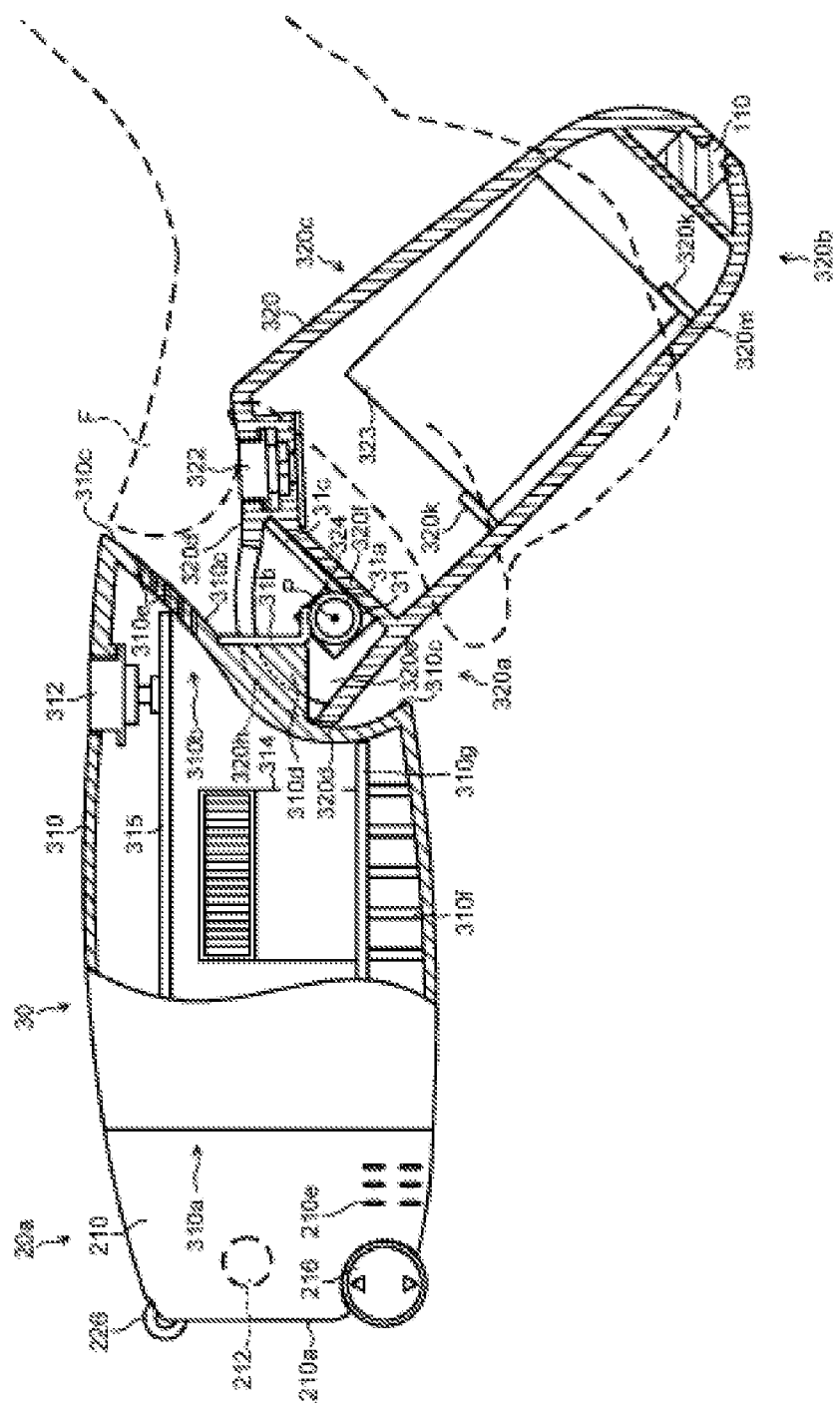
FIG. 11 is a schematic view schematically illustrating the light irradiation beauty device 3 after change of an angle.

Next, a light irradiation beauty device 3 of a third embodiment of the present invention is described with reference to FIG. 9 to FIG. 11. FIG. 9 is a plan view in which the light irradiation beauty device 3 is viewed with an operation unit 312 at the front. FIG. 10 is a partial cross-sectional view of the light irradiation beauty device 3 illustrating an A-A cross section of FIG. 9. FIG. 11 illustrates an A-A cross section of FIG. 1 and is a schematic view illustrating the light irradiation beauty device 3 after change of an angle. The dashed line of FIG. 11 illustrates a user's hand.

Hereinafter, the same constituent components as the constituent components of the first and second embodiments illustrated in FIG. 1 to FIG. 8 and each modification are designated by the same reference numerals and descriptions thereof are omitted.

As illustrated in FIG. 9, the light irradiation beauty device 3 includes a light irradiation unit 20a, a device body 30 (support unit), and a hinge 31.

(Light Irradiation Unit 20a)

The light irradiation unit 20a is a modification of the light irradiation unit 20 illustrated in FIG. 3. As illustrated in FIG. 10, the arrangement of the vents 210e included in the light irradiation unit 20 is changed. Other configurations and functions of the light irradiation unit 20a are the same as those of the light irradiation unit 20.

(Device Body 30)

The device body 30 includes a first chassis unit 310 (first body unit) and a second chassis unit 320 (second body unit). The device body 30 corresponds to the device body 10 illustrated in FIG. 1.

(First Chassis Unit 310)

The first chassis unit 310 includes a tip end portion 310a and a rear end portion 310b. In the first chassis unit 310, an operation unit 312, a cooling fan 314, and a control board 315 are disposed.

The tip end portion 310a corresponds to the tip end portion 10a illustrated in FIG. 1. To the tip end portion 310a, the light irradiation unit 20a is detachably attached (connected). Although not shown, a holding mechanism for holding the light irradiation unit 20a and a contact terminal electrically connected to the light irradiation unit 20a are provided in the tip end portion 310a.

The rear end portion 310b includes a facing surface 310c. In the rear end portion 310b, a hinge connection unit 310d and vents 310e are provided. The rear end portion 310b is located in a boundary unit with the second chassis unit 320.

The facing surface 310c faces the second chassis unit 320. The facing surface 310c is an inclined surface and is inclined toward a skin contact surface of the light irradiation unit 20a at a predetermined angle (for example, 10° or larger). The facing surface 310c is farthest from the skin contact surface in an area proximate to the operation unit 312 and approaches the skin contact surface as the facing surface 310c is inclined toward the cooling fan 314.

The hinge connection unit 310d projects from the facing surface 310c toward the second chassis unit 320. The hinge connection unit 310d is inserted into the second chassis unit 320. To the hinge connection unit 310d, a part of the hinge 31 is attached.

The vents 310e correspond to the vents 10d illustrated in FIG. 1. The vents 310e are through-holes extending from the facing surface 310c toward the inside of the first chassis unit 310. Through the vents 310e, wind (see "Air" in FIG. 10) for cooling the xenon tube 212 included in the light irradiation unit 20a passes.

Each vent 310e may be provided as an inlet hole or may be provided as an exhaust hole so long as it is configured to allow the passage of the wind.

Between the vents 310e and the second chassis unit 320, a small clearance is provided (see the reference numeral "c" in FIG. 1). This prevents the vents 310e from being closed by the second chassis unit 320.

The operation unit 312, the cooling fan 314, and the control board 315 are attached to the first chassis unit 310 by screws, adhesion, holding units, and the like, which are not shown. The "holding units" are columns 310f and a pedestal 310g, for example, provided in the first chassis unit 310.

The operation unit 312 corresponds to the operation unit 112 illustrated in FIG. 1. Herein, the operation unit 312 is a switch for turning ON or OFF a main power source. The operation unit 312 is provided in a side surface unit (part connecting the tip end portion 310*a* and the rear end portion 310*b*) of the first chassis unit 310.

The cooling fan 314 corresponds to the cooling fan 114 illustrated in FIG. 1. The cooling fan 314 generates the wind for cooling the xenon tube 212.

The control board 315 corresponds to the control board 130 illustrated in FIG. 1. The control board 315 controls the driving of the cooling fan 314 and the light emission of the xenon tube 212 or detects an operation of the operation unit 312 by a user.

(Second Chassis Unit 320)

The second chassis unit 320 includes a tip end portion 320*a*, a rear end portion 320*b*, and a side surface unit 320*c* (holding). In the second chassis unit 320, an operation switch 322, a capacitor 323, and a sensor unit 324 are disposed. The second chassis unit 320 can also include vents corresponding to the vents 310*e* of the first chassis unit 310.

The second chassis unit 320 is attached to the first chassis unit 310 through the hinge 31 and rotates relative to the first chassis unit 310. In other words, the first chassis unit 310 and the second chassis unit 320 are openably connected to each other by the hinge 31.

It is desirable that the length from the tip end portion 320*a* to the rear end portion 320*b* of the second chassis unit 320 and the length from the tip end portion 310*a* to the rear end portion 310*b* of the first chassis unit 310 are substantially equal to each other.

The tip end portion 320*a* includes a facing surface 320*d*. In the tip end portion 320*a*, a hinge housing unit 320*e*, a hinge connection unit 320*f*, a switch housing unit 320*g*, and a through-hole 320*h* are provided. The tip end portion 320*a* is located in a boundary unit with the first chassis unit 310.

The facing surface 320*d* faces the facing surface 310*c* of the first chassis unit 310. The facing surface 320*d* is an inclined surface and is inclined toward the skin contact surface at a predetermined angle (for example, 10° or larger).

The hinge housing unit 320*e* is a space housing the hinge 31. In the hinge housing unit 320*e*, the hinge connection unit 310*d* of the first chassis unit 310 is arranged.

The hinge connection unit 320*f* is provided such that the surface is exposed to the hinge housing unit 320*e*. The hinge connection unit 320*f* is a columnar member provided in the hinge housing unit 320*e* or a wall surface surrounding the hinge housing unit 320*e*. To the hinge connection unit 320*f*, a part of the hinge 31 is attached.

The switch housing unit 320*g* is a space housing the operation switch 322. The switch housing unit 320*g* is provided in the facing surface 320*d*.

The through-hole 320*h* communicates with the hinge housing unit 320*e* from the facing surface 320*d*. The hinge connection unit 310*d* of the first chassis unit 310 is inserted into the hinge housing unit 320*e* through the through-hole 320*h*.

The rear end portion 320*b* corresponds to the rear end portion 10*b* illustrated in FIG. 1. In the rear end portion 320*b*, the terminal unit 110 is disposed.

The operation switch 322 and the capacitor 323 are attached to the second chassis unit 320 by screws, adhesives, holding units, and the like, which are not shown. The "holding units" are columns 320*k* and a pedestal 320*m*, for example, provided in the second chassis unit 320.

The operation switch 322 and the capacitor 323 are electrically connected to the terminal unit 11, the control board 315 of the first chassis unit 310, or the xenon tube 212 of the light irradiation unit 20*a* by wiring, which is not shown.

Wiring from the second chassis unit 320 toward the first chassis unit 310 is disposed to pass-through—the vicinity of the hinge 31, for example, so as not to be disconnected by relative rotation of the first chassis unit 310 and the second chassis unit 320. Such wiring is commonly used in a notebook personal computer or the like.

The operation switch 322 is provided in the switch housing unit 320*g*. The operation switch 322 is electrically connected to the control board 315. In the operation switch 322, a state where the operation switch 322 is housed in the device body 30 (see FIG. 10) or a state where the operation switch 322 is exposed on the outside of the device body 30 (see FIG. 11) is switched by the relative rotation of the first chassis unit 310 and the second chassis unit 320.

As illustrated in FIG. 11, a user can depress the operation switch 322 when it is exposed on the outside of the device body 30 with the thumb, for example (see reference numeral F of FIG. 11). When the operation switch 322 is depressed, the xenon tube 212 emits light.

The operation switch 322 is arranged to be horizontal at least to the facing surface 320*d* in the vicinity of the operation switch 322. Since the facing surface 320*d* is inclined toward the skin contact surface as described above, the operation switch 322 is also inclined toward the skin contact surface at a fixed angle as a whole.

The capacitor 323 stores power required for the light emission of the xenon tube 212.

The hinge 31 includes a base unit 31*a*, a first connection portion 31*b*, and a second connection portion 31*c*.

The first connection portion 31*b* and the second connection portion 31*c* are provided in the base unit 31*a* to be rotatable relative to each other with a center axis P of the base unit 31*a* as the rotation axis.

As the hinge 31, a hinge that stably stops at an arbitrary angle can be used. A hinge having such a function is referred to as a torque hinge or a free stop hinge, for example.

The first connection portion 31*b* is attached to the hinge connection unit 310*d* of the first chassis unit 310. The second connection portion 31*c* is attached to the hinge connection unit 320*f* of the second chassis unit 320.

When the first connection portion 31*b* and the second connection portion 31*c* rotate relative to each other by 90°, for example, the first chassis unit 310 and the second chassis unit 320 also rotate relative to each other by 90° corresponding thereto.

FIG. 10 illustrates a state where the first connection portion 31*b* and the second connection portion 31*c* are closest to each other. In this state, the opening angle (relative angle in the rotation direction) of the second connection portion 31*c* to the first connection portion 31*b* is 0°.

When a user applies force to the first chassis unit 310 and the second chassis unit 320 such that the opening angle of the second connection portion 31*c* to the first connection portion 31*b* increases, the first chassis unit 310 and the second chassis unit 320 rotate relative to each other with the center axis P as the rotation axis, as illustrated in FIG. 11.

When the user releases the force, the rotation of the first connection portion 31*b* and the second connection portion 31*c* (first chassis unit 310 and second chassis unit 320) stops. The hinge 31 holds the opening angle between the first connection portion 31*b* and the second connection portion 31*c* (first chassis unit 310 and second chassis unit 320) at the time when the user releases the force until the user applies force to the first chassis unit 310 and the second chassis unit 320 subsequently.

The first connection portion 31b and the second connection portion 31c may rotate in a direction indicated by an arrow Ar of FIG. 9.

When the light irradiation beauty device 3 is pushed or pulled on the skin surface or pressed against the skin surface, it is desirable that the hinge 31 has such hardness in a rotation direction (rotational resistance strength) that the first connection portion 31b and the second connection portion 31c do not rotate relative to each other.

The light irradiation beauty device 3 may include a lock mechanism of detecting that the light irradiation beauty device 3 is pushed or pulled on the skin surface or pressed against the skin surface by a sensor to prevent the rotation of the hinge 31. As the lock mechanism, a mechanism of blocking the rotation of the hinge 31 by an electromagnetic valve using a solenoid is considered, for example.

The sensor unit 324 is a position sensor that detects the opening angle between the first connection portion 31b and the second connection portion 31c.

The sensor unit 324 outputs a detection result (for example, a digital signal indicating a value of the angle or analog signal generated by a current or a voltage) to the control board 315.

The sensor unit 324 has a rotary encoder, for example. The rotary encoder is attached to the hinge 31 and detects the rotation angle of the second connection portion 31c based on the first connection portion 31b.

The sensor unit 324 may have an illuminance sensor. The illuminance sensor measures the illuminance in the hinge housing unit 320e, for example. The measured illuminance is converted into the opening angle between the first chassis unit 310 and the second chassis unit 320.

The sensor unit 324 may detect not the opening angle between the first connection portion 31b and the second connection portion 31c, but the opening angle between the first chassis unit 310 and the second chassis unit 320. As the sensor unit 324, a Hall sensor may be provided.

(Control Board 315)

Figure 12:
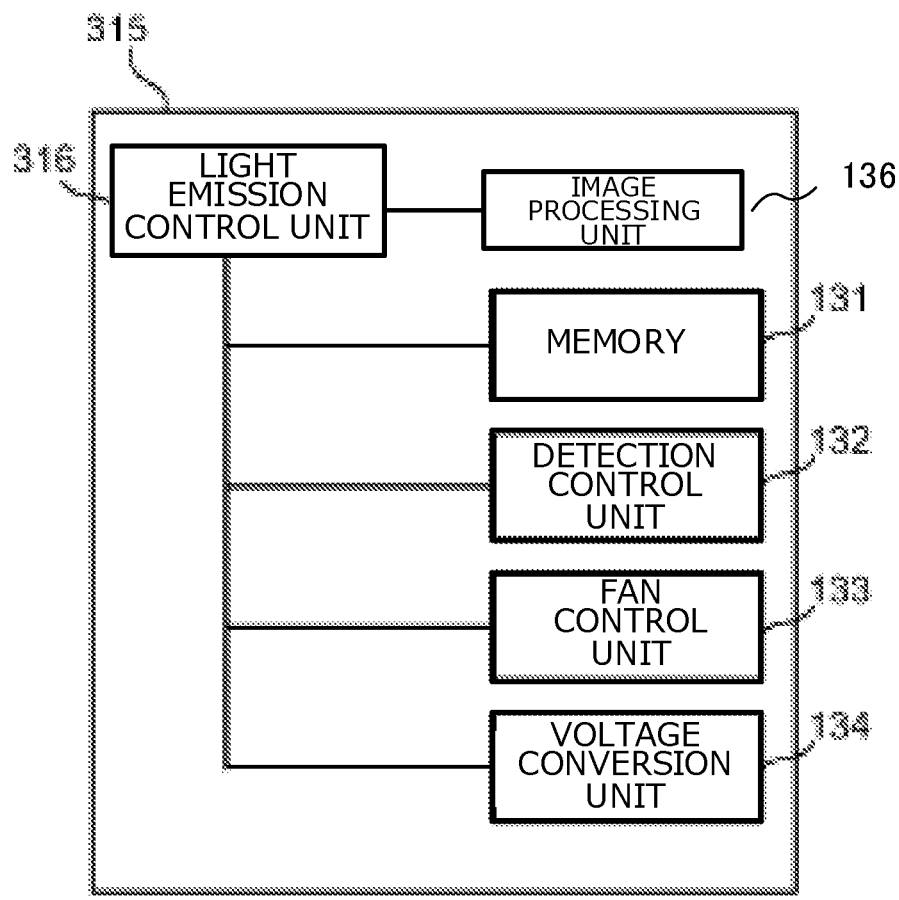
FIG. 12 is a functional block diagram of a control board 315.

Next, a function of the control board 315 is described using FIG. 12. FIG. 12 is a functional block diagram of the control board 315. The control board 315 corresponds to the control board 130 illustrated in FIG. 1.

The control board 315 has the memory 131, the detection control unit 132, the fan control unit 133, the voltage conversion unit 134, the image processing unit 136, and a light emission control unit 316 (light emission pattern switching unit).

These functions are realized by a control circuit formed by circuit elements (for example, IC chips for calculation and memory, resistive element, capacitor, and coil element).

The light emission control unit 316 corresponds to the light emission control unit 135. The light emission control unit 316 calculates the opening angle between the first connection portion 31b and the second connection portion 31c (or between the first chassis unit 310 and the second chassis unit 320) based on a calculation result output from the sensor unit 324.

An example of the calculation is conversion of a detection result (for example, current value, voltage value, or illuminance value) output from the sensor unit 324 into an angle with reference to a conversion table stored in the memory 131. When the detection result is a digital signal indicating an angle value, the conversion step can be omitted.

The light emission control unit 316 switches light emission patterns of the xenon tube 212 corresponding to the opening angle.

Further, the light emission control unit 316 may control the light emission based on skin feature information generated in the image processing unit 136. Specifically, in light of the fact that the absorption amount of absorbed and irradiated light increases as the skin color is deeper, at least one of the intensity of irradiation light, emission angle (size of a skin region to be irradiated), emission timing, and wavelength is adjusted such that the absorption amount is a predetermined value even when the color tone varies for each user or each skin surface. The adjustment is preferably carried out for each light emission timing.

<Light Emission Pattern Example>

(1) First Light Emission Pattern (Opening Angle: 0°)

When the opening angle between the first connection portion 31b and the second connection portion 31c is 0° as illustrated in FIG. 10, the light emission control unit 316 causes the xenon tube 212 to emit light such that the light emission pattern is the same as that of the first or second embodiment or each modification. More specifically, the light emission control unit 316 causes the xenon tube 212 to emit light corresponding to the rotation of the main roller 220.

(2) Second Light Emission Pattern (Opening Angle: 45° or Larger)

When the opening angle between the first connection portion 31b and the second connection portion 31c is 45° or larger as illustrated in FIG. 11, the light emission control unit 316 causes the xenon tube 212 to emit light only when the operation switch 322 is depressed without causing the xenon tube 212 to emit light corresponding to the rotation of the main roller 220. In this case, when the operation switch 322 is depressed once, the xenon tube 212 emits light once.

(3) Third Light Emission Pattern (Opening Angle: Larger than 0° and Smaller than) 45°

When the opening angle between the first connection portion 31b and the second connection portion 31c is larger than 0° and smaller than 45°, the light emission control unit 316 causes the xenon tube 212 to emit light continuously when the operation switch 322 is depressed without causing the xenon tube 212 to emit light corresponding to the rotation of the main roller 220. In this case, when the operation switch 322 is depressed once, the xenon tube 212 emits light a plurality of times.

(4) Modification of Light Emission Control

The opening angle serving as the condition that the xenon tube 212 is caused to emit light in the first light emission pattern is not limited to 0°. A configuration may be acceptable in which, when the opening angle is 0° or larger and 15° or smaller, for example, the xenon tube 212 is caused to emit light in the first light emission pattern.

Patterns corresponding to the opening angles may be classified in more detail. The patterns classified in more detail can be differentiated by varying the interval from light emission to the next light emission, the number of times of light emission, or the light emission intensity of the xenon tube 212.

When the light emission intensity of the xenon tube 212 is varied, the xenon tube 212 is controlled so that the light emission intensity in a case of the first pattern is lower than that in the other light emission patterns, the light emission intensity in a case of the second light emission pattern is the highest among the light emission patterns, and the light emission intensity in a case of the third light emission pattern is intermediate intensity, for example.

Further, during the period while the operation switch 322 is depressed, the xenon tube 212 continuously emits light (continuously repeats blinking). When the operation switch 322 is not depressed, the light emission of the xenon tube 212 may be stopped.

Further, the xenon tube 212 may be caused to emit light corresponding to the rotation of the main roller 220 during the period while the operation switch 322 is depressed.

In any of the patterns described above, it is desirable that, when the skin surface of a user does not contact the circumference of the opening 210*b* of the light irradiation unit 20*a*, the xenon tube 212 is not caused to emit light.

The light irradiation beauty device 3 configured as described above can reduce inconveniences of the operation in the depilation treatment.

The light irradiation beauty device 3 in the aspect in which the opening angle between the first connection portion 31*b* and the second connection portion 31*c* is 0° as illustrated in FIG. 10 can obtain the same effects as those of the first and second embodiments and each modification.

The light irradiation beauty device 3 can adjust the opening angle between the first chassis unit 310 and the second chassis unit 320 to an angle at which a user most easily holds the light irradiation beauty device 3 according to a skin surface to be subject to the depilation treatment by the hinge 31 (improvement of operability in depilation treatment).

In order to effectively irradiate the skin surface of a depilation treatment target with the light of the xenon tube 212, it is desirable that the opening 210*b* of the light irradiation unit 20*a* abuts on the skin surface in a horizontal state to the extent possible to the skin surface.

When abutting the skin surface as described above, the angle formed by the first chassis unit 310 and the skin surface is necessarily a substantially right angle.

It is easy to set the angle formed by the first chassis unit 310 and the skin surface to a right angle by moving up or down or extending or contracting a shoulder or an elbow or rotating a wrist. However, a human body has a large number of curved surfaces and the distance from a shoulder to the skin surface to be depilated also varies, and therefore a burden is imposed on a shoulder, an elbow, or a wrist depending on a skin surface, the hair of which a user may wish to remove.

Therefore, depending on a skin surface, the hair of which a user may wish to remove, a burden on an elbow or a wrist is reduced when the first chassis unit 310 and the second chassis unit 320 are linearly arranged (the opening angle between the first chassis unit 310 and the second chassis unit 320 is about 180°) as illustrated in FIG. 10, or a burden on a shoulder and an elbow or a wrist are reduced when the first chassis unit 310 and the second chassis unit 320 rotate relative to each other as illustrated in FIG. 2 in some cases.

For example, in the depilation of a skin surface where there is a long flat continuous surface as compared with other skin surfaces of a body and which is distant from a shoulder of a hand holding the light irradiation beauty device, such as a leg or an arm, a burden on a shoulder, an elbow, or a wrist are reduced when the first chassis unit 310 and the second chassis unit 320 are linearly arranged, and operability of the light irradiation beauty device 3 generally is enhanced.

In the depilation of a skin surface that has a narrow area and that is close to a shoulder holding the light irradiation beauty device 3 as compared with a leg, an arm, and the like, such as an armpit or a face, a burden on a shoulder, an elbow, or a wrist are reduced when the second chassis unit 320 rotates to the first chassis unit 310 and the operability of the light irradiation beauty device 3 is good in many cases.

Further, also in the depilation of a part in a dead angle for a user, such as a back or a neck, burdens to a shoulder, an elbow, or a wrist are reduced when the second chassis unit 320 rotates to the first chassis unit 310 and the operability of the light irradiation beauty device 3 is good in many cases.

The light irradiation beauty device 3 can change the angle of the second chassis unit 320 to the first chassis unit 310 corresponding to the position of the skin surface to be depilated, and therefore can perform the depilation treatment of various body parts in a good operative state.

According to the light irradiation beauty device 3, when the first chassis unit 310 and the second chassis unit 320 rotate relative to each other, the operation switch 322 is exposed as illustrated in FIG. 11. Since the operation switch 322 is arranged in the second chassis unit 320 and is located near a user's finger, the user can easily depress the operation switch 322.

Further, the operation switch 322 is inclined to the skin contact surface at a predetermined angle as a whole. The inclination facilitates the touch of the operation switch 322 to a user's finger and the depression of the operation switch 322.

The light irradiation beauty device 3 switches the light emission patterns of the xenon tube 212 corresponding to the direction and the angle of the second connection portion 31*c* to the first connection portion 31*b*, and therefore a user does not need to switch the light emission patterns by a button operation. As a result, the operability relating to the switching of the light emission patterns of the xenon tube 212 is improved.

According to the light irradiation beauty device 3, the vents 310*e* are provided in the rear end portion 310*b* including the facing surface 310*c* of the first chassis unit 310. When the first chassis unit 310 and the second chassis unit 320 are linearly arranged as illustrated in FIG. 10, the vents 310*e* are covered by the tip end portion 320*a* of the second chassis unit 320 such that a user's finger does not touch the vents 310*e*.

Therefore, the airflow in the first chassis unit 310 is blocked by a user's finger, so that the cooling of the xenon tube 212 can be stably performed.

Between the vents 310*e* and the second chassis unit 320, a small clearance is provided. This prevents the vents 310*e* from being closed by the second chassis unit 320.

The facing surface 310*c* is inclined to be separated from a user's finger (for example, thumb F of FIG. 11) holding the second chassis unit 320 as illustrated in FIG. 11. This can prevent the vents 310*e* from being closed by the user's finger.

As a result, the airflow in the first chassis unit 310 is blocked by the user's finger, so that the cooling of the xenon tube 212 can be stably performed.

(Modification 2)

The light irradiation beauty device 3 can be variously modified.

For example, a click hinge capable of stepwise changing the angle may be adopted as the hinge 31. For example, the device body 30 and the light irradiation unit 20*a* may be formed integral with each other. Body hair may be removed by a laser in place of the light emission of the xenon tube 212. The light irradiation unit 20*a* may have a Peltier device to warm or cool the skin surface. The main roller 220 may contain one or more rollers having any of a cylindrical shape, a polygonal columnar shape, or a spherical shape, for example.

A configuration may be acceptable in which the light irradiation unit 20a has an electrode and applies a current to the skin surface for the purpose of moving muscles to forcibly contract the muscles. The forcible contraction of muscles by a current is referred to as Electrical Muscle Stimulation (EMS).

The current is desirably an alternating current and the frequency is not particularly limited.

Further, the elements of the first to third embodiments and each modification can be combined as appropriate or some configurations thereof can also be omitted.

DESCRIPTION OF REFERENCE NUMERALS 1, 2, 3 light irradiation beauty device
10, 30 device body
20, 20a light irradiation unit
31 hinge
110 terminal unit
112, 312 operation unit
114, 314 cooling fan
130, 315 control board
131 memory
132 detection control unit
133 fan control unit
134 voltage conversion unit
135 light emission control unit
136 image processing unit
316 light emission control unit
210 chassis
212 xenon tube
214 transparent glass
220 main roller
221 board
222, 223 shaft holding stand
224 rotation shaft
290 auxiliary roller
240 imaging unit
230 detection unit
231 holding unit
232a, 232b detection target
233, 333a, 333b sensor
310 first chassis unit
320 second chassis unit
322 operation switch
323 capacitor
324 sensor unit
330 detection unit

The invention claimed is:

1. A beauty device comprising:
a chassis;
a plurality of rollers comprising a first roller and a second roller on different sides of the chassis, the different sides being a front side and a first surface, wherein
the first roller is fixed to the chassis on the front side and at least a part of the first roller is configured to contact skin and a center of the first roller has a different diameter from an end portion of the first roller, and
the second roller is fixed partially within the chassis on the first surface and at least a part of the second roller is configured to contact with the skin;
an irradiation unit configured to irradiate the skin with light; and
a control unit configured to control the irradiation unit based on a rotation of the rollers,
wherein the first surface of the chassis is configured to contact the skin and the front side of the chassis extends from the first surface away from the skin.

2. The beauty device according to claim 1, wherein:
the irradiation unit includes a rectangular window through which an emitted light passes, and
a rotation shaft of each of the first roller and the second roller is provided in parallel to a longitudinal direction of the window.

3. The beauty device according to claim 2, wherein:
the first roller and the second roller are provided in opposing relation with the window, wherein the window is interposed between the first roller and the second roller, and
the control unit configured to control the irradiation unit based on a rotation of the first roller.

4. The beauty device according to claim 3, wherein:
the first roller has a diameter increasing from the center toward to the end portion of the first roller.

5. The beauty device according to claim 4, wherein:
the second roller has a diameter decreasing from a center toward an outside of the second roller.

6. The beauty device according to claim 1, wherein:
a height to a surface, of the first roller is greater than a height to the surface of the second roller, wherein the surface is configured to contact the skin.

7. The beauty device according to claim 1, further comprising:
a sensor configured to detect a color of the skin, wherein the control unit is further configured to control an intensity of irradiation of light based on a detected color.

8. The beauty device according to claim 1, further comprising:
a device body, wherein
the device body comprises a tip end portion, a rear end portion, a partition, an exhaust port, an inlet port, a cooling fan, and a touch sensor.

9. The beauty device according to claim 8, wherein:
the irradiation unit is detachably attached to the tip end portion of the device body.

10. The beauty device according to claim 8, wherein:
the exhaust port penetrates from a front surface of the device body to a rear surface of the device body, and
the inlet port penetrates from a front surface of the partition to a rear surface of the partition.

11. The beauty device according to claim 8, wherein:
the cooling fan is configured to draw air from outside of the device body into the device body through the irradiation unit and inlet port, and exhaust the air out of the device body through the exhaust port.

12. The beauty device according to claim 1, further comprising:
an imaging device comprising a camera, a lens, a light receiving element, and an image processing processor, and
the imaging device is configured to acquire image data, process the image data and output an image processing result.

13. The beauty device according to claim 8, wherein:
the touch sensor is configured to output a signal indicating a pressure or an absence of contact with the skin.

14. The beauty device according to claim 1, wherein:
the first roller comprises a sensor configured to measure the rotation of the first roller.

15. A beauty device comprising:

a device body;

an irradiation device that is detachably attached to the device body and configured to irradiate skin with light, the irradiation device comprising:

a chassis;

a plurality of rollers comprising a first roller and a second roller on different sides of the chassis, the different sides being a front side and a first surface, the first roller being fixed to the chassis on the front side and at least a part of the first roller being configured to contact the skin, the first roller having a diameter that increases from a center toward an outside of the first roller, and the second roller being fixed partially within the chassis on the front surface and at least a part of the second roller being configured to contact with the skin, the second roller having a diameter that decreases from a center toward an outside of the second roller; and a controller configured to control the irradiation device to irradiate the skin based on a rotation of the first roller and the second roller wherein the first surface of the chassis is configured to contact the skin and the front side of the chassis extends from the first surface away from the skin.

16. The beauty device according to claim 15, wherein:

the device body comprises a tip end portion, a rear end portion, a partition, an exhaust port, an inlet port, a cooling fan, and a touch sensor, and the irradiation device is detachably attached to the tip end portion of the device body.

17. The beauty device according to claim 16, wherein:

the touch sensor is configured to output a signal indicating a pressure or an absence of contact with the skin.

18. The beauty device according to claim 15, further comprising:

an imaging device comprising a camera, a lens, a light receiving element, and an image processing processor, and the imaging device is configured to acquire image data, process the image data and output an image processing result.

19. The beauty device according to claim 15, wherein:

the first roller comprises a sensor configured to measure the rotation of the first roller.

20. The beauty device according to claim 1, wherein the front side of the chassis extends orthogonally from the first surface away from the skin.

* * * * *